US010881606B2

(12) United States Patent
Schmitz et al.

(10) Patent No.: US 10,881,606 B2
(45) Date of Patent: *Jan. 5, 2021

(54) COMPOSITION FOR TRANSDERMAL DELIVERY OF CATIONIC ACTIVE AGENTS

(75) Inventors: Christoph Schmitz, Rheinbrohl (DE); Mohammad Sameti, Bonn (DE); Andreas Koch, Melsbach (DE); Michael Horstmann, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/737,209

(22) PCT Filed: Jun. 16, 2009

(86) PCT No.: PCT/EP2009/004316
§ 371 (c)(1),
(2), (4) Date: Dec. 16, 2010

(87) PCT Pub. No.: WO2009/153019
PCT Pub. Date: Dec. 23, 2009

(65) Prior Publication Data
US 2011/0111029 A1 May 12, 2011

Related U.S. Application Data

(60) Provisional application No. 61/132,527, filed on Jun. 19, 2008.

(51) Int. Cl.
A61K 9/00 (2006.01)
A61K 9/70 (2006.01)
A61K 47/32 (2006.01)
A61K 47/12 (2006.01)
A61K 31/00 (2006.01)

(52) U.S. Cl.
CPC .......... A61K 9/0009 (2013.01); A61K 9/7023 (2013.01); A61K 31/00 (2013.01); A61K 47/12 (2013.01); A61K 47/32 (2013.01)

(58) Field of Classification Search
CPC combination set(s) only.
See application file for complete search history.

(56) References Cited

U.S. PATENT DOCUMENTS

| 222,276 | A | 12/1879 | Hunter |
| 486,902 | A | 11/1892 | Shults |
| 5,558,633 | A | 9/1996 | Phipps et al. |
| 5,685,837 | A | 11/1997 | Horstmann |
| 5,993,849 | A | 11/1999 | Assmus et al. |
| 6,048,545 | A | 4/2000 | Keller et al. |
| 6,745,071 | B1 | 6/2004 | Grace et al. |
| 8,366,600 | B2 * | 2/2013 | Sebree .................. A61K 9/0009 600/20 |
| 2003/0078646 | A1 * | 4/2003 | Axelgaard ........... A61N 1/0472 607/142 |
| 2004/0101550 | A1 | 5/2004 | Windt-Hanke et al. |
| 2004/0242770 | A1 | 12/2004 | Feldstein et al. |
| 2008/0221170 | A1 * | 9/2008 | Roberts et al. ............... 514/351 |

FOREIGN PATENT DOCUMENTS

| EP | 0898962 A1 | 3/1999 |
| EP | 1080731 | 3/2001 |
| EP | 0813879 B1 | 10/2002 |
| WO | WO 98/01111 A1 | 1/1998 |
| WO | WO 2002/30402 | 4/2002 |
| WO | WO 2004/093786 A2 | 11/2004 |
| WO | WO 2005/039531 | 5/2005 |
| WO | WO 2007/120747 A2 | 10/2007 |
| WO | WO 2007/147043 A2 | 12/2007 |
| WO | WO 2008/027218 A2 | 3/2008 |

OTHER PUBLICATIONS

Bradley et al., Br J Pharmacol. Mar. 1974; 50(3): 345-354.*
Banga et al., J. Controlled Release, vol. 7, Issue 1, Apr. 1988, 1-24. (Year: 1988).*
Luzardo-Alvarez, A., et al.; Iontophoretic Delivery of Ropinirole HCl: Effect of Current Density and Vehicle Formulation,: "Proceedings of the International Symposium on Controlled Release of Bioactive Materials"; 27th Ed., pp. 159-160 (2000).
N.F. Villarino, et al., "Transdermal Drug Administration: A Therapeutical Alternative," Analecta Veterinaria, (2006) vol. 26 (1), pp. 28-37. (abstract in English).
M. Yoshida, et al., "Effects of Application Voltage and Cathode and Anode Positions at Electroporation . . . ," Chem. Pharm. Bull, (2000) vol. 48 (11), pp. 1807-1809.

* cited by examiner

Primary Examiner — Robert S Cabral
(74) Attorney, Agent, or Firm — ProPat, LLC; Cathy R. Moore; Vinisha Joshi

(57) ABSTRACT

A composition for transdermal delivery, particularly iontophoretic transdermal delivery, having at least one cationic active agent or a salt thereof. The composition comprises at least one cationic active agent or a salt thereof, at least one polyamine and/or polyamine salt, water or an aqueous solvent mixture, and optionally one or more additives. Use of the composition as a component of a transdermal patch or of an iontophoretic transdermal patch is also provided, as well as the use of the composition in a method for transdermally or iontophoretically administering cationic active agents. A method for determining the in vitro skin permeation properties of an active agent-containing iontophoretic composition is also provided.

28 Claims, 1 Drawing Sheet

COMPOSITION FOR TRANSDERMAL DELIVERY OF CATIONIC ACTIVE AGENTS

CROSS-REFERENCE TO RELATED APPLICATIONS

This application is a National Stage application of International Application No. PCT/EP2009/004316, filed on Jun. 16, 2009, which claims priority of U.S. provisional application Ser. No. 61/132,527, filed on Jun. 19, 2008, both of which are incorporated herein by reference in their entireties.

BACKGROUND OF THE INVENTION

Field of the Invention

The present invention relates to transdermal delivery of cationic active agents. More specifically, the present invention relates to compositions suitable for transdermal delivery, in particular for iontophoretic transdermal delivery, of cationic active agents.

Description of the Prior Art

The transdermal route of parenteral administration provides many advantages over other routes of administration. Methods and devices for administering drugs through the skin are well known in the field of pharmaceuticals. Typically, transdermal administration is effected by using passive transdermal systems (e.g. Transdermal Therapeutic Systems, TTS) which deliver drug substances through the skin at defined rates by diffusion processes. Therefore, transdermal drug delivery is very inefficient for certain types of drug substances. In particular, ionized drugs are often unable to passively permeate through the skin at therapeutically effective rates.

The process of iontophoresis was originally described by LeDuc in 1908, and even earlier in U.S. Pat. No. 222,276 (1879) and U.S. Pat. No. 486,902 (1892). Since then, iontophoresis has found commercial use in the delivery of ionically charged therapeutic drug molecules such as pilocarpine, lidocaine, dexamethasone, lidocaine and fentanyl.

Generally, iontophoresis is a delivery method which relies on the basic principle that application of electric current can provide external energy to enable or enhance the passage of drug ions across the skin, presumably by increasing drug permeability through the membranes of the skin. When ions bearing a positive charge (e.g. cationic active agents) are placed into or under the anode of an iontophoretic system, these ions will then—upon application of current—be forced to move away from the anode and, following the direction of the electrical field, towards the cathode which is placed on an adjacent skin area. During this process, transport of the cationic drug through the skin is enhanced or facilitated. Iontophoresis may be used with different forms of active pharmaceutical ingredients, most favourably with those carrying an electrical charge, which are thus directly moved across barriers (e.g. the skin) within an electrical field.

In iontophoresis, different to diffusion-controlled transdermal delivery described above, the skin contact area of the device and the active ingredient concentration within the device are less important with respect to the level of skin flux of the active ingredient. The delivery of active ingredient through the skin is largely dependent on the applied current by which the active ingredient can be forced into the skin.

A typical iontophoretic drug delivery system includes an electrolytic electrical system comprising an anode and a cathode to be adhered to different—preferably adjacent—skin areas of a patient, each electrode being connected by a wire to a remote power supply, generally a microprocessor-controlled electrical instrument. Such types of such devices have been published, including systems with a lean construction (e.g. U.S. Pat. No. 5,685,837 or 6,745,071) as well as more sophisticated systems, which systems are basically known to the expert. Iontophoretic transdermal systems for lidocain and fentanyl are introduced into the US market.

For the application of drugs, liquid or gelled aqueous formulations have been already incorporated (e.g. U.S. Pat. No. 5,558,633) into iontophoretic devices. However, in such devices, iontophoretic delivery of pharmaceutical actives may be impaired due to, for instance, the presence of "background" electrolytes (see, for instance, Luzardo-Alvarez, A., et al., Proceedings of the International Symposium on Controlled Release of Bioactive Materials (2000), $27^{th}$ Ed., pp. 159-160). Regarding the construction of iontophoretic devices, there is a lack of pharmaceutical gels or liquids which are devoid of contributing "background" counter ions.

Furthermore, due to adverse properties of certain polymeric structures, the use of polymers in iontophoretic devices frequently results in an impaired constancy of drug delivery. Although an adhesive comprising an amino group-containing methacrylate copolymer and dicarboxylic or tricarboxylic acids was describe for dermal or transdermal therapy systems in U.S. Pat. No. 5,993,849, the suitability of such mixture in an iontophoretic composition was not recognized in this prior art document.

Various pharmaceutical active substances exhibit side effects—such as impairment of renal or hepatic function—that may be caused when these drugs are administered orally. Hence, in these cases, parenteral administration is desirable as this route of administration is less prone to cause said side effects. On the other hand, for the treatment of many diseases or disease symptoms, it is of critical importance to produce a rapid onset of action in order to obtain instant therapeutic effects, e.g. pain relieve. Therefore, transdermal administration by using transdermal therapeutic systems (TTS) is out of question in such circumstances since these administration forms rely on passive diffusion which results in a slow onset of action and a "lag time" of considerable length (1 hour or longer). In addition, in the case of cationic active substances, transdermal transport by passive diffusion is generally very inefficient. Therefore, a conventional TTS that would be capable of rapidly delivering a therapeutically effective dose of such an active substance is not feasible.

However, iontophoresis has an inherent risk of causing side effects such as skin irritation, erythemas, burning sensations or even skin necrosis, in particular, when the current intensity is increased or when iontophoresis is continued over extended time periods. On the other hand, increasing current intensity may be desirable in order to allow for the administration of higher doses of therapeutic agents, since the amount of drug ions that are transported iontophoretically is directly proportional to the amount and time of applied current. Generally, the intensity of the current should not exceed 600 $\mu A/cm^2$, in order to avoid burning sensations or skin burns. The output voltage is generally in the range of 0.5 to 10 V, depending on the resistance between the two electrodes and the intermediate skin area, which may amount to 50 k$\Omega$ or higher.

Transdermal drug transport by iontophoresis is a complex process which may be affected by a variety of parameters, such as the concentration of electrolytes, ionic strength, the type, composition and viscosity of the electrode material, the duration of iontophoresis, skin resistance, or area size of the electrodes. In general, little is known about the various influences of these parameters on the iontophoretic process.

Furthermore, in order to meet the strict galenic requirements, transdermal iontophoretic devices must contain defined electrolyte concentrations having defined ionic strengths, in order to ensure that the active substance is transported into the skin at a desired and constant rate, and to ensure that the transdermally administered dose is both safe and therapeutically effective.

To meet these requirements, iontophoretic devices are usually provided with electrode reservoirs containing a mixture of dissolved active substances (drug substances) and additional electrolytes (e.g. salts such as NaCl, as well as buffer substances). Thus, it is at least in principle possible to obtain electrolyte concentrations and ionic strengths that are sufficiently high. However, due to their small size and mobility, these ionic additives are transported relatively rapidly from the electrode compartment to the skin. As a consequence, the electrode compartment will become depleted of electrolytes, and ionic strength will decrease. This will eventually cause the electrical field to collapse, which renders the iontophoretic device unreliable and difficult to control. This is of particular importance in the case of active substances (i.e. drug substances) having a high specific activity or a narrow therapeutic index, as the patients would be exposed to severe security risks.

SUMMARY OF THE PRESENT INVENTION

In view of the above, it is therefore one major object of the present invention to provide compositions that are suitable for transdermal delivery, particularly iontophoretic transdermal delivery, of at least one cationic active agent. More specifically, it is an object of the present invention to provide compositions which permit efficient, rapid-onset and safe transdermal iontophoretic delivery of cationic active agents.

It is a further object of the present invention to provide compositions suitable for use in transdermal delivery, particularly for use in iontophoretic transdermal delivery, of at least one cationic active agent, while reducing or eliminating the aforementioned disadvantages, in particular, depletion of electrolytes and concomitant decrease of electrical field strength.

In view of the above objects, the present invention provides improved compositions for transdermal delivery, particularly for iontophoretic transdermal delivery, of at least one cationic active agent.

The present invention is based, at least in part, on the surprising observation that the incorporation of polyamines or polyamine salts into an iontophoretic reservoir composition, which is particularly in the form of an aqueous (liquid or gelled) skin-contacting composition, results in an enhanced efficiency in the iontophoretic transdermal delivery of cationic therapeutically active agents, without causing any significant fluctuations or drops in active substance delivery or without causing substantial skin irritation.

By using a composition according to the present invention as an anodic drug reservoir of an iontophoretic patch, efficiency of iontophoretic transdermal delivery can be improved by increasing the electric current while avoiding the disadvantages discussed above. For example, the polyamine-containing compositions of the present invention allows for the use of up to 4 mA/cm$^2$ of current without causing significant erythema to subjects undergoing such treatment.

In one embodiment, the invention pertains to a composition for transdermal delivery of at least one cationic active agent or a salt thereof, comprising:

said at least one cationic active agent or a salt thereof,
at least one polyamine or/and polyamine salt,
water or an aqueous solvent mixture; and
optionally, one or more additives.

In a further embodiment, the above-mentioned composition is a hydrogel. In further embodiments, the above-mentioned aqueous composition or hydrogel is absorbed to an absorbent material In a further embodiment, the polyamine-containing composition further comprises at least one acid selected from the group comprising fatty acids and dicarboxylic acids.

In a further embodiment, the composition is an adhesive, preferably a self-adhesive, composition which has skin-adhesive properties.

In a further embodiment, the composition comprises an alkylated methacrylate polyamine copolymer, between 0.5 and 10%-wt. of at least one cationic active agent or salt thereof, between 0.02 and 0.5%-wt. methyl para-hydroxybenzoate, between 1.0 and 5.0%-wt. lauric acid, and between 0.05 and 0.75%-wt. adipic acid, and said composition has a water content of at least 80%-wt.

In a further embodiment, the composition comprises 4 to 7%-wt. alkylated methacrylate polyamine copolymer, 3 to 5%-wt. of at least one cationic active agent or salt thereof, 1 to 5%-wt. lauric acid, 0.05 to 0.75%-wt. adipic acid, 0.05 to 0.75%-wt. methyl para-hydroxybenzoate, 84 to 88%-wt. water.

The invention further encompasses the use of said composition as a component of a transdermal patch or as a component of an iontophoretic transdermal patch.

The invention further encompasses the use of said composition in a method for transdermally or iontophoretically administering cationic active agents to subjects requiring treatment with such active agents.

Further embodiments are described in the "Detailed Description" below.

The compositions of the present invention are generally useful in connection with therapeutically active agents having a cationic structure, particularly active agents carrying amino or imino groups. Accordingly, the present invention is useful for transdermally (particularly by iontophoretic methods) administering analgesics such as fentanyl or morphine, antiemetics such as granisetrone, or other drug compounds acting on the central nervous system such as rivastigmine or galanthamine.

When used for transdermal delivery of active substances, the composition of the present invention serves as a matrix or reservoir from which said at least one cationic active agent is released to the skin and then permeates through the skin, either passively or by iontophoresis.

DETAILED DESCRIPTION OF THE PRESENT INVENTION

Figure 1:
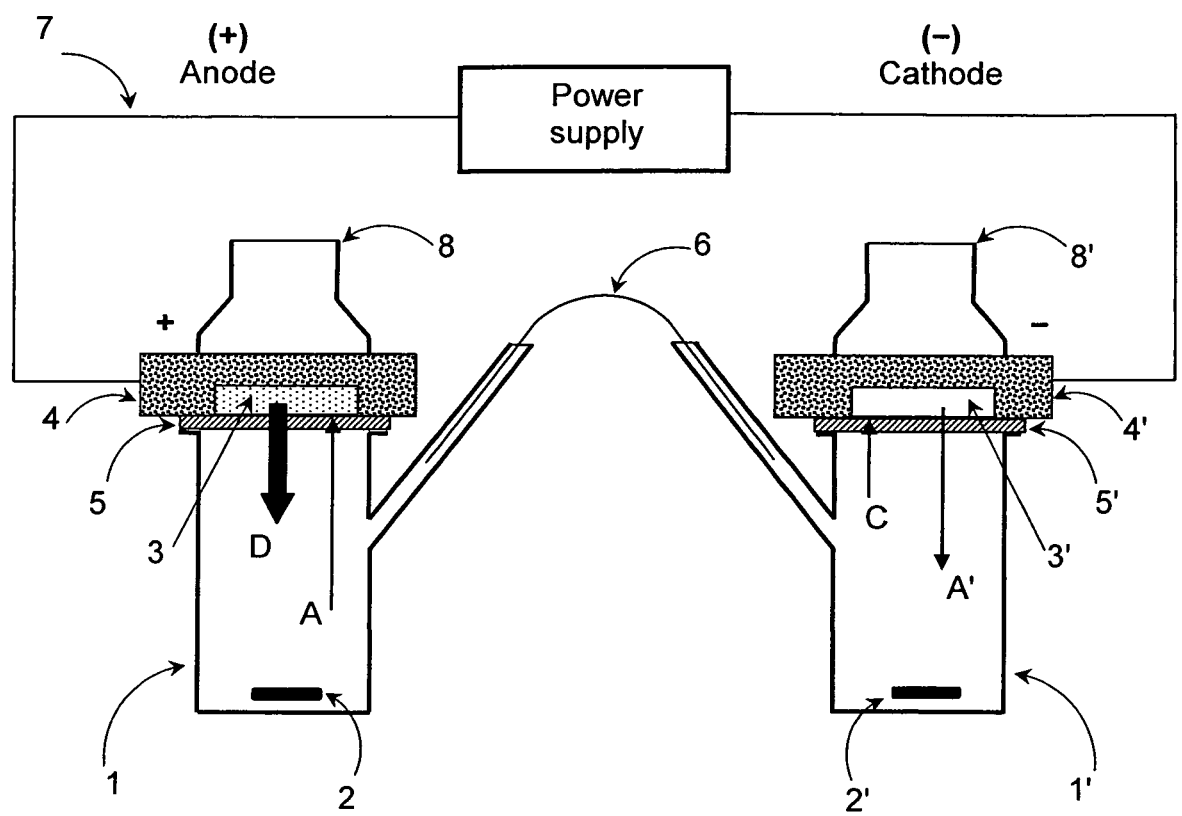
FIG. 1 is a schematic representation of an experimental iontophoretic setup for determining in vitro skin permeation obtainable with a cationic active substance-containing composition in accordance with the present invention.

The invention pertains to compositions suitable for transdermal, particularly iontophoretic delivery of at least one cationic active agent or a salt thereof.

The term "cationic active agents" generally relates to active agents which are present as positively charged ions (cations), or which are capable of forming positive charges in aqueous media. For example, many biologically active agents have functional groups that are readily convertible to a positive ion or that can dissociate into a positively charged ion and a counter ion in an aqueous medium, e.g. soluble salts of basic active agents.

The term "active agents" particularly includes therapeutically active agents, pharmacologically active agents, and other agents having beneficial effects when administered to a human being or animal. Generally, the term "active agents" includes drug substances or medicinal active agents. The term "active agents" further includes agents for use in veterinary medicine.

The compositions according to the present invention comprise water or an aqueous solvent mixture. Preferably, the proportion of water or solvent mixture is at least 15%-wt., more preferably 40%-wt., relative to the total weight of the composition. According to a further embodiment, the water content or the proportion of said solvent mixture is in the range of 80 to 99%-wt.

The term "aqueous solvent mixture" generally includes liquid mixtures containing water and at least one further solvent which is generally selected from polar, water-miscible solvents such as, for instance, alcohols (e.g. ethanol, isopropanol, glycerol).

The term "polyamine" particularly includes cationic organic compounds having at least two positively charged groups, preferably amino groups selected from the group comprising primary amino groups, secondary amino groups and tertiary amino groups. The invention also includes polyamines comprising, for instance, pyrrolidino, piperidino or morpholino groups.

Generally, the polyamines used in accordance with the present invention preferably include polyelectrolytes which are polymers or macromolecules comprising two or more positive charges upon being dissolved in water or an aqueous solvent. Since the positive charges are immobilized on the polyamine compounds which, due to their size, are immobilized in the composition or have only reduced mobility, these ionic additives are substantially prevented from being transported to the skin or to the counter electrode when the composition is used in a iontophoretic administration method. Thus, a decrease of ionic strength can be prevented, and the iontophoretic process can be maintained over extended time periods while maintaining efficient transdermal absorption.

According to one embodiment of the invention, the polyamine(s) is/are preferably selected from the group comprising acrylate copolymers, methacrylate copolymers, alkylated acrylate copolymers and alkylated methacrylate copolymers. These copolymers contain two or more amino groups as defined above.

The alkyl group is preferably selected from $C_1$ to $C_{12}$ alkyl groups (linear or branched), such as, for instance, methyl, ethyl, propyl, isopropyl, butyl. The alkylated copolymers may also include hydroxylated alkyl groups, preferably $C_1$ to $C_{12}$ hydroxyalkyl groups, such as, for instance, hydroxymethyl, hydroxyethyl or hydroxypropyl.

Concerning the polyamines, a preferred amino group is the "diamino ethyl" moiety present within an organic compound, preferably within a polymeric organic compound.

More preferred polyamines are polymeric polyamines including, for instance, methacrylate copolymers such as copolymers of butylated or/and methylated methacrylate(s) and dimethyl aminoethyl methacrylate. The preferred copolymers include the "basic butylated methacrylate copolymer" described in the Pharmacopoea Europaea (Ph. Eur.), the "amino methacrylate copolymer" described in the USP/NF, and the "aminoalkyl methacrylate copolymer E" described in "Japanese Pharmaceutical Excipients". Such copolymers are commercially available under the trademark EUDRAGIT® (from Evonik Industries, formerly Degussa), for instance, EUDRAGIT® RL 100, EUDRAGIT® RL PQ, EUDRAGIT® RS 100, EUDRAGIT® RS PQ, EUDRAGIT® E 100. EUDRAGIT® E 100 is particularly preferred as a polyamine compound to be used in the compositions of the present invention. EUDRAGIT® E 100 is a cationic copolymer based on dimethylaminoethyl methacrylate, butylmethacrylate, and methyl methacrylate. The average molecular weight of this polymer is approx. 150,000.

Generally, any polyamines containing at least two amino groups as defined above may be used in the compositions of the present invention, provided that they are toxicologically safe and suitable for use in pharmaceutical products.

Polyamines useful for producing the compositions of the present invention may further be selected from the group comprising cyclic and macrocyclic polyamines, such as cyclen, polyamines based on the aziridine monomer, such as polyethylene imines, as well as polyethylene amines, putrescine, cadaverine, spermidine, spermine, as well as polypropyleneimine, polyvinylamine, polyvinylimine, polyvinylimidazol, polyvinylpyridine, and polyguanidines. Preferably, the polyamine compounds of the present invention have a molecular mass of 1500 or above.

In a further embodiment, the composition of the present invention comprises a combination of at least two different polyamine compounds selected from the polyamine compounds defined above.

Preferably, the polyamine compounds to be used in accordance with the compositions of the invention are present in the form of polyamine salts, particularly water-soluble polyamine salts. Suitable salts are obtainable by combining or reacting the above-mentioned polyamines with suitable acids, preferably organic acids, by standard procedures.

Preferably, the proportion of said polyamine(s) or polyamine salt(s) is in the range of 1 to 25%-wt., more preferably 5 to 20%-wt., particularly 10 to 18%-wt., relative to the total weight of the composition. In further embodiments, the composition may comprise 3.0 to 10.0%-wt., or 4.0 to 9.0%-wt., or 5.0 to 8.0%-wt., or 5.0 to 6.0%-wt., or about 5.86% of an alkylated methacrylate copolymer described above, e.g. a butylated methacrylate copolymer such as EUDRAGIT® E 100.

The cationic active agent to be incorporated into the polyamine-containing composition is preferably selected from one or more of the following groups of cationic active agents:

opioid agonists, including analgesics such as fentanyl, sufentanyl, morphine, morphine derivatives such as codeine or heroine, dihydrocodeine, hydromorphone, oxycodone, hydrocodone, pethidine, loperamide, diphenoxylate, methadone, tramadole, tilidine;

opioid antagonist such as naloxone, naltrexone;

mixed opiate agonists/antagonists, such as buprenorphine, pentazocine, nalbuphine;

antiemetics including 5-$HT_3$ receptor antagonists such as granisetron, lerisetron, ondansetron, dolasetron, metoclopramid, as well as antidopaminergic drugs such as domperidone, as well as H1 receptor antagonists such as promethazine or meclozine, as well as muscarinic antagonists such as scopolamine;

drug compounds acting on the central nervous system such as rivastigmine, galanthamine, tacrine, donepezil; as well as pramipexol, epinephrine, dopamine, ropinirole, nicotine, fluphenazine, chlorpromazine, benzodiazepines, monoamine reuptake inhibitors such as amitriptyline, antidepressants such as mianserin;

alkaloids such as ergotamine, dihydroergotamine, methysergide or lisuride, belladonna alkaloids;

peptides, particularly peptide hormones or blood clotting factors;

cationic active indole compounds such as N-dimethyltryptamine or psilocin;

local anesthetics such as lidocaine, buprivacaine, articaine, procaine;

gastrointestinal disease therapeutics, such as carnitine chloride, metoclopramide;

skeletal muscle relaxants such as vancuronium bromide;

antibiotics such as tetracyclins, tetracyclin-based preparations, kanamycine, kanamycine-based preparations, gentamycine, gentamycine-based preparations, quinine;

weight-reduction agents such as fenfluramine or ephedrine;

antidiabetics such as metformine;

inhibitors of thrombocyte aggregation, e.g. ticlopidine or clopidogrel;

antiarrhythmics such as quinidine or lidocaine;

cardioactive or cardiovascular agents such as dopamine, norepinephrine, methoxamine, epinephrine, verapamil, diltiazem, propranolol, clonidine, tolazoline;

sympathomimetics such as salbutamole or terbutaline;

antihistaminics such as clemastine, cetirizine or chlorphenoxamine.

In a preferred embodiment, the active agent(s) is/are selected from the group of cationic indole compounds, particularly from the group of cationic indole compounds comprising N-dimethyltryptamine and psilocin; said groups also including pharmaceutically acceptable salts of said cationic active indole compounds.

In general, the compositions of the present invention are useful for all kinds of active agent compounds having a cationic (aminic) structure.

In a further embodiment, the composition comprises at least one active agent selected from the group comprising opioids, other central nervous system (CNS)-active compounds, and peptides having a cationic charge.

The cationic active agent(s) may also be present in the form of pharmaceutically acceptable salts. Examples of pharmaceutically acceptable salts include, but are not limited to, chloride, bromide, iodide, sulfuric, phosphate, lactate, citrate, tartrate, salicylate, succinate, maleate, gluconate, mesylate, laurate, dodecylate, myristate, palmitate, stearate, coconoate, behinate, oleate, linoleate, linolenate, eicosapentaenoate, eicosahexaenoate, docosapentaenoate, docosahexaenoate, eicosanids and the like.

According to further embodiments, the anodic reservoir composition contains 0.1 to 20%-wt., or 0.2 to 10%-wt., or 2 to 10%-wt., or 3 to 5%-wt., or 0.1 to 0.5%-wt. of said cationic active substance(s), or salt(s) thereof.

Although the compositions of the present invention are particularly suitable for use in combination with cationic active agents, these compositions can be used in combination with other types of active agents as well. Hence, the present invention also encompasses compositions in which said at least one cationic active agent is replaced by at least one active agent having neutral charge or by an anionic active agent. Further, the present invention also encompasses compositions in which comprise said at least one cationic active agent in combination with at least one further active agent which is selected from the group comprising active agents having a neutral charge and anionic active agents. Generally, the active agents to be included in the compositions of the present invention are agents which are capable of penetrating the skin by passive diffusion or by chemical enhancer-mediated skin permeation, or, in particular, by iontophoretic skin permeation.

In further embodiments of the present invention, the composition further comprises at least one acid which is preferably selected from the group comprising fatty acids and dicarboxylic acids.

However, other types of organic acids may also be used, as, for instance, acids selected from hydroxy alkanoic acids or from tricarboxylic acids.

By combining the above-discussed polyamine(s), e.g. amino group-containing polyacrylate copolymers, with one or more acids preferably selected from the group of fatty acids and dicarboxylic acids, the corresponding polyamine salts are obtained. These polyamine salts are generally water-soluble and, upon dissolution in water, form a polymeric electrolyte. Furthermore, the present compositions comprising said polyamine salts have been found to be particularly suitable as a carrier or reservoir for ionic, dissociated active agents in iontophoretic devices.

Further, it was surprisingly found that by combining polyamine(s) with one or more of said acids in the presence of water, hydrogels can easily be obtained which are particular useful to serve as reservoir compositions in iontophoretic systems.

The term "fatty acids" particularly includes aliphatic monocarboxylic acids having an aliphatic tail comprising up to 30 C atoms, which acids may be linear or branched, saturated or unsaturated. Preferably, $C_6$ to $C_{14}$ saturated fatty acids are used. Fatty acids that may be used in accordance with the present invention include, for instance, hexanoic acid, decanoic acid, lauric acid, myristic acid, palmitic acid, caprylic acid and stearic acid; lauric acid being preferred.

The term "dicarboxylic acid" generally includes organic compounds that are substituted with two carboxylic acid functional groups, which compounds include linear, branched and cyclic compounds, which compounds may be saturated or unsaturated. For instance, the dicarboxylic acid may be selected from dicarboxylic fatty acids, particularly from $C_4$ to $C_{10}$ dicarboxylic acids. Examples of fatty dicarboxylic acids include glutaric acid, adipic acid and pimelic acid; adipic acid being preferred.

In further embodiments, the composition may contain a combination comprising at least two fatty acids, or a combination comprising at least two dicarboxylic acids, or a combination comprising at least one fatty acid and at least one dicarboxylic acid.

Generally, the amount of fatty acid(s) or/and dicarboxylic acid(s) is adjusted so as to be at least sufficient to solubilize the polyamine(s), and/or other components present in said composition(s), in order to obtain a hydrogel composition having the desired properties, particularly semi-solid or solid consistency as well as skin-adhesive properties.

Preferably, the total amount of fatty acid(s) or/and dicarboxylic acid(s) in the composition is in the range of 0.1 to 15%-wt., particularly in the range of 0.5 to 10%-wt.

According to a further embodiment, the concentration of said fatty acid(s) is 0.1 to 10%-wt, preferably 0.5 to 7.0%-wt. According to a further embodiment, the concentration of said dicarboxylic acid(s) is 0.05 to 5%-wt., preferably 0.1 to 2.0%-wt.

In one embodiment, the composition comprises adipic acid in a concentration of between 0.1 and 2.0%-wt., or between 0.15 and 0.5%.-wt., or between 0.20 and 0.40%.-wt.

In further embodiments, lauric acid is selected as said fatty acid, and this fatty acid is present at a concentration of 0.5%-wt. to 7.0%-wt., or of 0.1 to 10%-wt., or 0.2 to 9.5%-wt., or 0.3 to 9.0%-wt., or 0.4 to 8.5%-wt., or 0.5 to 8.0%-wt., or 1.0 to 7.0%-wt., or 1.5 to 6.0%-wt., or 2.0 to 5.0%-wt., or 3.0 to 4.0%-wt., or at a concentration of about 3.40%-wt., relative to the total composition.

Preferably, the compositions are formulated as hydrogels including at least one gel-forming polymer (e.g. a polyamine salt as described above, and/or other gel-forming polymers as generally known in the field of pharmaceutical preparations), together with a gel-forming amount of water or aqueous solvent mixture.

Preferably, the relative amounts of water and gel-forming components are adjusted so as to obtain a hydrogel having solid or semi-solid consistency. However, the formulations of the present invention may also be formulated as liquids.

In a further embodiment, the hydrogel compositions may comprise additional gel-forming polymers which may be selected e.g. from the group consisting of polyacrylates or cellulose derivatives such as hydroxypropylmethyl cellulose, hydroxypropyl cellulose or hydroxyethyl cellulose.

The use of hydrogel formulations in iontophoresis is particularly advantageous since in this case the ionic strength can be adjusted by varying the proportion of water within the hydrogel. Thus, the ionic strength can be easily adjusted to optimize the efficacy of the iontophoretic process in each particular case.

Accordingly, in a further embodiment of the invention, the composition is a hydrogel containing said cationic active agent(s) or salt(s) thereof, said polyamine(s) or polyamine salt(s), water, and, optionally, said one or more additives. Preferably, said hydrogel further contains one or more additives selected from fatty acids and dicarboxlic acids as described above.

In a further embodiment, the composition is a hydrogel or a liquid aqueous composition which comprises an alkylated methacrylate polyamine copolymer, between 0.5 and 10%-wt. of at least one cationic active agent or salt thereof, between 0.02 and 0.5%-wt. methyl para-hydroxybenzoate, between 1.0 and 5.0%-wt. lauric acid, and between 0.05 and 0.75%-wt. adipic acid, and said hydrogel composition has a water content of at least 80%-wt.

In a further embodiment, the composition is a hydrogel or a liquid aqueous composition which comprises 4 to 7%-wt. alkylated methacrylate polyamine copolymer, 3 to 5%-wt. of at least one cationic active agent or salt thereof, 1 to 5%-wt. lauric acid, 0.05 to 0.75%-wt. adipic acid, 0.05 to 0.75%-wt. methyl para-hydroxybenzoate, 84 to 88%-wt. water.

In a further embodiment, the composition comprises 4.00%-wt. of cationic active agent(s), 86.37%-wt. of water, 5.86%-wt. of alkylated methacrylate copolymer (=polyamine), 3.40%-wt. of lauric acid, 0.27%-wt. of adipic acid, and 0.10%-wt. of methyl para-hydroxybenzoate, wherein each specified value may vary by ±10% relative to the indicated mean value.

As described above, the compositions of the present invention are formulated as aqueous compositions, particularly as hydrogel compositions. In a further embodiment, the said aqueous compositions have a pH of 3 to 8, preferably 5.5 to 7, or most preferably about 6.

Generally, it is preferred to adjust and maintain the pH in said water-containing compositions such they do not substantially affect the ph of the skin, when the compositions are applied to the skin (e.g. during transdermal or iontophoretic administration). In a further embodiment, the pH of the skin changes about ±4.0 or less, about ±3.5 or less, about ±3.0 or less, about ±2.5 or less, about ±2.0 or less, about ±1.5 or less, about ±1.0 or less, or about ±0.5 or less. Substances and buffers suitable for pH adjustment are known to the skilled person.

The composition according to the present invention may optionally contain one or more further additives. Said additives include, but are not limited to, additives selected from the group comprising solubility enhancers, skin permeation enhancers, preservatives and antimicrobial agents.

In this connection, the term "solubility enhancer" generally relates to compounds capable of increasing the solubility of the cationic active agent within the composition. This can be achieved either by modulating the possible interactions between said cationic active agent and the other components present in the composition, by additionally incorporating suitable excipients.

Alternatively, the solubility of the active agent can be achieved by changing its crystal modification. Examples of solubility enhancers include, without limitation, water; diols such as propylene glycol and glycerol; monoalcohols such as ethanol, propanol and higher alcohols; dimethylsulfoxide (DMSO), dimethylformamide, N,N-dimethylacetamide, N-substituted alkyl-azacycloalkyl-2-ones. As already described above, compounds selected from the groups of fatty acids and dicarboxylic acids are particularly effective for enhancing the solubility of the polyamine(s).

Further, the term "skin permeation enhancer" particularly includes compounds capable of increasing the permeability of the skin for an active agent contained in the composition, particularly for a cationic active agent. Due to this increase in skin permeability, the rate at which the active agent(s) permeate(s) through the skin and enter(s) the blood circulation is also increased. The enhanced permeation effected by the use of said skin permeation enhancers can be assayed and confirmed by measuring the rate of active agent diffusion through animal or human skin using a diffusion cell apparatus generally known in the art.

Examples of permeation enhancers include, but are not limited to, dimethylsulfoxide (DMSO), N,N-dimethylacetamide (DMA), decylmethylsulfoxide (C10 MSO), polyethylene glycol monolaurate (PEGML), propylene glycol (PG), propylene glycol monolaurate (PGML), glycerol monolaurate (GML), lecithin, the 1-substituted alkyl-azacycloalkyl-2-ones, particularly 1-n-dodecylcylazacycloheptan-2-one, alcohols, and the like. The permeation enhancer may also be selected from vegetable oils, e.g. safflower oil, cotton seed oil, or corn oil. Combinations comprising two or more different permeation enhancers may also be used.

Further, the term "antimicrobial agent" generally includes agents which are capable of preventing the growth of microbes in a pharmaceutical preparation, particularly in a composition according to the present invention. Examples of suitable antimicrobials include, but are not limited to, salts of chlorhexidine, such as iodopropynyl butylcarbamate, diazolidinyl urea, chlorhexidine digluconate, chlorhexidine acetate, chlorhexidine isethionate, chlorhexidine hydrochloride. Other cationic antimicrobial agents may also be used, such as benzalkonium chloride, benzethonium chloride, triclocarbon, polyhexamethylene biguanide, cetylpyridinium chloride, methylbenzethonium chloride.

Other antimicrobial agents include, but are not limited to, halogenated phenolic compounds, such as 2,4,4'-trichloro-2-hydroxy diphenyl ether (Triclosan), parachlorometa xylenol (PCMX); methyl para-hydroxybenzoate; and short-chain alcohols such as ethanol, propanol, and the like.

Preferably, the total concentration of said antimicrobial agent(s) is in the range of 0.01 to 2%-wt., relative to the total weight of the composition in which it is included.

In further embodiments, the composition comprises between 0.01 and 1.0%-wt., or between 0.05 and 0.5%-wt., or between 0.07 and 0.4%-wt., or between 0.08 and 0.3%-wt., or between 0.09 and 0.2%-wt., or about 0.10 of methyl parahydroxybenzoate.

The invention also includes embodiments in which said composition further comprises an adsorbent material that is soaked or impregnated with said composition which is generally a liquid aqueous composition or hydrogel composition. The adsorbent material which is soaked or impregnated with said aqueous or hydrogel composition(s) serves to keep said composition in place and, at the same time, to maintain the low-viscosity structure. Suitable adsorbent materials may be selected from fibrous pads, fabrics, sponges, tissues, non-woven or woven materials, felts or felt-like materials, etc.

According to a further embodiment, the composition of the present invention has adhesive properties, to ensure that the composition is maintained in direct and complete contact with the skin at the site of application during the whole time period of transdermal drug administration. Adhesiveness can be obtained by incorporating one or more adhesive polymers into said compositions. Adhesive polymers suitable for this purpose are generally known to the skilled person. Preferably, a polyamine or polyamine salt having adhesive properties is used as said adhesive polymer(s).

Preferably, the compositions of the present invention are self-adhesive. To render the compositions self-adhesive, they may further contain one or more additives selected from the group of tackifiers which group includes, but is not limited to, hydrocarbon resins, rosin derivatives, glycols (such as glycerol, 1,3-butanediol, propylene glycol, polyethylene glycol), and succinic acid.

The present invention further pertains to any embodiments of the present invention that may result from combining two or more of the above-described embodiments, or from combining one or more individual features that are mentioned throughout the above description with any one of the above-described embodiments of the present invention.

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

Generally, the compositions of the present invention can be manufactured by conventional methods. Broadly, the compositions of the present invention are obtainable by dissolving or dispersing the various ingredients (i.e. cationic active ingredient, polyamine, additives) in water or an aqueous solvent mixture. The resulting mixture may then be spread on a flat surface or poured into moulds or extruded, and then allowed to solidify to obtain hydrogel compositions having the desired shape. During these process steps, or after solidification, the composition may be combined with additional components as required to produce the final product, generally a pharmaceutical administration form.

However, various alternative methods for manufacturing the compositions of the present invention may be used, as will be readily realized by the skilled person.

The present invention further encompasses the use of the above-described composition(s) as an integral component of a transdermal patch or TTS. Preferably, such composition is incorporated into said patch or TTS during manufacture, to form the active substance reservoir of the patch or TTS.

Further, the present invention encompasses the use of the above-described composition(s) as an integral component of an iontophoretic patch, preferably as an anodic reservoir of the patch. Preferably, such composition is incorporated into said iontophoretic patch during manufacture, to form the anodic reservoir of the patch. The above-mentioned administration forms are obtainable by manufacturing methods generally known in the art.

The present invention further pertains to the use of the above-described composition(s) in methods of transdermally administering a therapeutically effective amount of at least one cationic active agent to a subject, particularly a patient in need of therapeutic treatment. Said methods further include iontophoretic methods for transdermal administration. Generally, the above-mentioned methods comprise a step of applying a composition according to the present invention to the skin of said subject, and allowing the active agent(s) contained in the composition to be released therefrom and to permeate through the skin and to enter the blood circulation of said subject. This process may be enhanced by iontophoresis.

The present invention further pertains to a method for determining the in vitro skin permeation properties (in particular, effectiveness of skin permeation) of an active agent-containing iontophoretic composition, comprising:

providing a first FRANZ diffusion cell;

providing a second FRANZ diffusion cell;

placing said first and second cells into a thermostatically controlled environment, preferably at 32° C.;

filling each cell with a liquid acceptor medium;

electrically connecting the liquid acceptor medium contained in the first cell with the acceptor medium contained in the second cell by means of an electrically conductive wire (e.g. silver wire) which is inserted into the interior of each cell;

placing said active agent composition on top of a human or animal membrane, preferably a skin (e.g. bovine udder skin), in the first FRANZ diffusion cell and covering said composition with an electrically conductive electrode material (e.g. a metallic or metal-coated foil);

connecting said electrode material to the anode of a direct current power supply if the active agent contained in said composition is a cationic active agent, or connecting said electrode material to the cathode of said power supply if the active agent contained in said composition is an anionic active agent;

placing an electrolyte-containing composition on top of a human or animal membrane, preferably a skin, in the second FRANZ diffusion cell and covering said composition with an electrically conductive electrode material;

connecting said electrode material to said power supply so as to close the circuit;

applying current from said power supply to said electrodes;

at regular time intervals, removing liquid samples from the acceptor medium of said first FRANZ diffusion cell, and determining the concentration of said active agent in said sample.

The FRANZ diffusion cells used in the method are generally known in the art and are conventionally used e.g. for determining skin permeation rates of transdermal therapeutic systems; these cells may be modified as required by the particular circumstances. As an acceptor medium, a physiological or isotonic buffer is preferably used.

Generally, the area size of said active agent-containing composition (test sample) and of the composition of the counter electrode (electrolyte-containing composition) should be the same. During the experiment, the amperage of the power supply should be adjusted to about 0.1 to 1.5 mA per square centimeter of said area size.

Upon determining the concentration of said active agent in said sample, the resulting values which correspond to the cumulated amounts of permeated active agents released from said composition can be compared with suitable reference samples.

The present invention further pertains to an experimental setup comprising two FRANZ cells, as essentially described above.

EXAMPLE

In the following, the invention and its effectiveness are illustrated by means of examples, together with the attached drawing.

FIG. 1 shows a schematic representation of an experimental iontophoretic setup for determining in vitro skin permeation obtainable with a cationic active substance-containing composition in accordance with the present invention.

The experimental setup shown in FIG. 1 includes an iontophoretic 2-chamber cell which comprises a first chamber (1) and a second chamber (1'). Both chambers are modified FRANZ diffusion cells which are conventionally used for determining in vitro permeation rates of transdermal therapeutic systems (TTS). As shown in FIG. 2, the FRANZ cells were modified and arranged so as to be suitable for determining the skin permeation profiles of a composition intended for use in an iontophoretic device, in accordance with the present invention.

The chambers (1,1') are immersed in a thermostatically controlled water bath (not shown; T=32° C.). Each of the chambers (1,1') is filled with isotonic phosphate buffer serving as the acceptor medium. This buffer is adjusted to pH 5.5 and contains 0.1% $NaN_3$ serving as a preservative. During the experiments, the temperature of the phosphate buffer is maintained essentially constant at 32° C. At the bottom of each chamber (1,1'), a magnetic stirring bar (2, 2') is provided for continuously mixing the acceptor medium.

In the in vitro permeation studies of the present invention, bovine udder skin was used (dermatomized to a layer thickness of 1200 μm) to serve as an "in vitro skin model".

Identical samples of said dermatomized bovine udder skin (5,5') were placed on top of each chamber (1,1'). Chamber (1) was connected to the anode of a power supply, and chamber (1') was connected to the cathode of this power supply. Both chambers were electrically connected by a silver wire (6) (acting as a "salt bridge") so as to obtain a closed electric circuit (7).

In anodic chamber (1), a drug reservoir (3) was placed on top of the bovine udder skin (5) and was then covered with a metallic backing layer (4). In this system, the drug reservoir (3) is a composition according to the present invention, which, for instance, may serve as the anodic reservoir of an iontophoretic device, in which the metallic backing layer (4) represents the anode of the said device. As a backing layer, any metallic backing layer may be used (e.g. such as used in transdermal therapeutic systems), or conventional Ag/AgCl-coated polymer foils may be used. The metallic backing layer is connected to the anode of the power supply by a wire. In the drug reservoir or composition (3), a salt of a cationic active agent was included as an active ingredient to be released therefrom.

The anodic reservoir (3) was prepared by applying a solution of said cationic active agent (4%-wt.) in polyamine (acrylic copolymer; EUDRAGIT® E 100) onto a non-woven viscose material (coating weight per unit area: 0.1 $g/cm^2$).

The area size of the anodic reservoir was 4 $cm^2$ in each case.

Similarly, a buffer reservoir (3') was placed on top of the bovine udder skin (5') of chamber (1'), and the buffer reservoir was covered with a metallic backing layer (4') as described above. In this case, the backing layer (4') is connected to the cathode of the power supply. Accordingly, the buffer reservoir (3') which is in contact with backing layer (4') serves as a cathodic reservoir of the experimental iontophoretic device, and backing layer (4') serves as the cathode of this iontophoretic device. The area size of the cathodic reservoir was 4 $cm^2$ in each case.

The reservoir (3') of the counter electrode (cathode) was composed of a 2% (per weight) solution of hydroxypropylmethyl cellulose in 0.9% (per weight) saline solution. This solution was applied onto a non-woven viscose material (coating weight per unit area: 0.1 $g/cm^2$).

On top of each backing layer (4,4'), a cover or lid (8,8') is placed and secured so that the chambers or cells (1,1') are essentially hermetically closed during the permeation experiments.

The power supply used in the setup shown in FIG. 1 works as a constant current source and was adjusted to a constant amperage of approximately 0.5 to 0.6 mA per square centimeter of permeated skin area. The power supply used in the experiments was a DC generator (HAMEG HM 7042-5, from HAMEG Instruments GmbH, Mainhausen, Germany). In all experiments, iontophoresis was continued over a total time period of three hours.

Upon application of current, the drug cations permeated through the bovine udder skin into the acceptor medium, as indicated by arrow (D) in FIG. 1. This could be determined by removing samples from the acceptor medium at regular time intervals, and analyzing the active agent content in the individual samples.

Similarly, the counter ions (e.g. $Na^+$, $Cl^-$) migrate from the acceptor medium into the corresponding electrode reservoir, as indicated by arrows (A) and (C) in FIG. 1.

During the iontophoretic process, there was also a transport of anions from buffer reservoir (3') into the acceptor medium of cathodic chamber (1'), as indicated by arrow (A') in FIG. 1.

TABLE 1

| Formulation No. | Gel-forming Component | Conc. of gel component [%-wt.] | Conc. of active agent salt [%-wt.] | Water [%-wt.] |
|---|---|---|---|---|
| 1, 1' | Gelatine (Ph. Eur.) | 15 | 4 | 81 |
| 2, 2' | Hydroxypropyl-methylcellulose (HPMC) | 1 | 4 | 95 |
| 3, 3' | Acrylic copolymer* + fatty acids** | 10 | 4 | 86 |

*-EUDRAGIT® E 100
**Lauric acid (3%-wt.) + adipic acid (0.5%-wt.).

All formulations contain 0.1% Nipagine (para-hydroxybenzoic acid ester) as preservative.

Formulations 3 and 3' are compositions in accordance with the invention. Formulations 1, 1' and 2, 2' are reference compositions. In the case of the reference examples (1', 2', 3'), the experiments was performed using the same corresponding galenic preparations (1, 2, 3), but without applying electric current. The permeation results obtained with the polyamine-containing formulation (3) according to the invention were found to be markedly superior to the results obtained with reference formulations (1, 2) based on gelatine or HPMC, respectively.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

We claim:

1. A self-adhesive transdermal patch composition for iontophoretic transdermal delivery of at least one cationic active agent or a salt thereof, comprising:
    said at least one cationic active agent or a salt thereof, wherein the total content of said at least one cationic active agent or a salt thereof amounts to 0.1 to 20%-wt. relative to the total weight of the transdermal patch composition, and wherein said at least one cationic active agent is selected from the group consisting of cationic indole compounds and salts thereof;
    at least one polyamine having two or more amino groups in the form of a polyamine salt having adhesive properties, wherein said polyamine salt is obtained by combining or reacting said at least one polyamine with at least one fatty acid in combination with at least one dicarboxylic acid and wherein said at least one polyamine includes cationic organic compounds having at least two positively charged groups;
    water or an aqueous solvent mixture, wherein the proportion of water or aqueous solvent mixture is in the range of 80-99%-wt. relative to the total weight of the transdermal patch composition; and
    optionally, one or more additives;
    wherein said transdermal patch composition is a polymeric electrolytic hydrogel matrix based on (i) polymer consisting of said amino-group-containing polyamine whose amino group-moieties consist of dimethylamino ethyl methacrylate, (ii) said fatty acid, (iii) said dicarboxylic acid and (iv) said water or aqueous solvent mixture alone, with said cationic active agent and said optional additive(s) contained therein
    said transdermal patch composition is absorbed on an absorbent material; and
    said hydrogel comprises between 0.5%-wt. and 7.0%-wt. of lauric acid as fatty acid and between 0.1%-wt. and 2.0%-wt. of adipic acid as dicarboxylic acid.

2. The self-adhesive transdermal patch composition according to claim 1, wherein said at least one polyamine in the form of a polyamine salt is/are selected from the group consisting of salts of polymeric polyamines and salts of macrocyclic polyamines.

3. The self-adhesive transdermal patch composition according to claim 1, wherein said at least one polyamine in the form of a polyamine salt is/are selected from the group consisting of salts of acrylate copolymers and salts of methacrylate copolymers.

4. The self-adhesive transdermal patch composition according to claim 3, wherein said methacrylate copolymers comprise alkylated methacrylate copolymers.

5. The self-adhesive transdermal patch composition according to claim 1, wherein the proportion of said at least one polyamine in the form of a polyamine salt is in the range of 1 to 25%-wt. relative to the total weight of the composition.

6. The self-adhesive transdermal patch composition according to claim 1, wherein the concentration of said fatty acid is 1.0 to 5.0%-wt.

7. The self-adhesive transdermal patch composition according to claim 1, wherein the concentration of said dicarboxylic acid is 0.1 to 0.75%-wt.

8. The self-adhesive transdermal patch composition according to claim 1, wherein said transdermal patch composition is a self-adhesive composition and said hydrogel is formed with additives consisting of fatty acid and dicarboxylic acid.

9. The self-adhesive transdermal patch composition according to claim 1, wherein said cationic indole compounds comprise N-dimethyltryptamine and psilocin, and pharmacologically acceptable salts of said cationic indole compounds.

10. The self-adhesive transdermal patch composition according to claim 1, wherein said at least one cationic active agent is selected from opioids, other central nervous system (CNS)-active compounds, or peptides having a cationic charge.

11. The self-adhesive transdermal patch composition according to claim 1, wherein said hydrogel matrix has a pH in the range of 3 to 8.

12. The self-adhesive transdermal patch composition according to claim 11, wherein said hydrogel matrix has a pH in the range of 6 to 7, and said polyamine consists of aminoalkyl methacrylate copolymer.

13. The self-adhesive transdermal patch composition according to claim 1, wherein said one or more additive additives is/are selected from the group consisting of solubility enhancers, skin permeation enhancers and antimicrobial agents.

14. The self-adhesive transdermal patch composition according to claim 1, and further comprising:
    an alkylated methacrylate polyamine copolymer;
    between 0.5 and 10%-wt. cationic active agent or a pharmaceutically acceptable salt thereof;
    between 0.02 and 0.5%-wt. methyl para-hydroxybenzoate as additive;
    between 1.0 and 5.0%-wt. lauric acid; and
    between 0.1 and 2.0%-wt. adipic acid, wherein said transdermal patch composition has a water content of at least 80%-wt.

15. The self-adhesive transdermal patch composition according to claim 14, consisting of:
    4 to 7%-wt. alkylated methacrylate polyamine copolymer;
    3 to 5%-wt. cationic active agent;
    1 to 5%-wt. lauric acid;
    0.1 to 0.75%-wt. adipic acid;
    0.05 to 0.75%-wt. methyl para-hydroxybenzoate; and
    84 to 88%-wt. water.

16. The self-adhesive transdermal patch composition according to claim 15, wherein said cationic active agent is selected from the group consisting of indole compounds.

17. The self-adhesive transdermal patch composition according to claim 5, wherein the proportion of said at least one polyamine in the form of a polyamine salt is in the range of 5 to 20%-wt. relative to the total weight of the composition.

18. The self-adhesive transdermal patch composition according to claim 17, wherein the proportion of said at least one polyamine in the form of a polyamine salt is in the range of 10 to 18%-wt. relative to the total weight of the transdermal patch composition.

19. The self-adhesive transdermal patch composition according to claim 6, wherein the concentration of said fatty acid(s) is 0.5 to 7.0%-wt.

20. The self-adhesive transdermal patch composition according to claim 7, wherein the concentration of said dicarboxylic acid(s) is 0.1 to 2.0%-wt.

21. The self-adhesive transdermal patch composition according to claim 12, wherein said hydrogel matrix has a pH in the range of 6 to 6.5.

22. The self-adhesive transdermal patch composition according to claim 1, wherein said polyamine salt has self-adhesive properties.

23. The self-adhesive transdermal patch composition according to claim 1, wherein the cationic active agent is present in an amount ranging from 3 to 20 wt %. and 80 to 88 wt % water.

24. The self-adhesive transdermal patch composition according to claim 1, wherein the absorbent material is selected from fibrous pads, fabrics, sponges, tissues, non-woven materials, woven materials or felts.

25. The self-adhesive transdermal patch composition according to claim 1, wherein said transdermal patch composition is self-adhesive and disposed on a metallic backing layer connected to the power supply by a wire.

26. The self-adhesive transdermal patch composition according to claim 1, wherein said polyamine is a basic butylated methacrylate copolymer, amino methacrylate copolymer or amino alkyl methacrylate copolymer E.

27. The self-adhesive transdermal patch composition according to claim 1, wherein said transdermal patch composition does not comprise glycerol.

28. A self-adhesive transdermal patch composition according to claim 25, wherein said hydrogel composition exhibits a solid or semi-solid consistency and the absorbent material is selected from the group consisting of fabrics, sponges, tissues, non-woven material, woven material and felts.

* * * * *